United States Patent [19]

Leavitt

[11] 4,383,039

[45] May 10, 1983

[54] L-PROLINE PRODUCTION FROM ALGAE

[75] Inventor: Richard I. Leavitt, Baton Rouge, La.

[73] Assignee: Ethyl Corporation, Richmond, Va.

[21] Appl. No.: 329,227

[22] Filed: Dec. 10, 1981

[51] Int. Cl.$^3$ ............................ C12P 13/24; C12R 1/89
[52] U.S. Cl. ........................................ 435/107; 435/946
[58] Field of Search ................................ 435/107, 946

[56] References Cited

U.S. PATENT DOCUMENTS 3,650,068  3/1978  Meyer et al. ............................ 47/1.4
4,224,409  9/1980  Nakamori et al. ...................... 435/107

FOREIGN PATENT DOCUMENTS 1132036  10/1968  United Kingdom .

OTHER PUBLICATIONS

Aust. J. Plant Physiology, 1979, vol. 6, pp. 69–79.
Limnol. Oceanographer, vol. 10, pp. 192–206 (1965).

*Primary Examiner*—Lionel M. Shapiro
*Attorney, Agent, or Firm*—Donald L. Johnson; John F. Sieberth; Willard G. Montgomery

[57] ABSTRACT

A process for recovering L-proline from Chlorella sp. 580 algae without disrupting the L-proline synthesizing capability of the algae thereby permitting reuse of the proline depleted cells to produce additional amounts of L-proline. The process comprises cultivating Chlorella sp. 580 algae under high-intensity illumination in an aqueous growth medium containing a high concentration of sodium chloride (at least 1 M in the final stage of cultivation), providing an adequate supply of carbon, in a depth not exceeding approximately 20 cm of the aqueous medium, until algae of high L-proline content are obtained, harvesting the algae and thereafter diluting the harvested algae with water to a concentration below at least 0.3 M NaCl to effect the release of L-proline from the algae into the aqueous phase, removing the algae from the L-proline containing aqueous solution and reintroducing the algae into a high salt concentration containing medium of up to at least 1 M NaCl to restimulate L-proline production within the algae.

20 Claims, No Drawings

L-PROLINE PRODUCTION FROM ALGAE

BACKGROUND OF THE INVENTION

This invention relates to a process for producing L-proline. In particular, it relates to a process for the production of L-proline in high yields by cultivation and work-up of a certain type of algae, specifically, Chlorella sp. 580. More particularly, it relates to a process for recovering L-proline from the algae cells without disrupting or destroying the capability of the cells to resynthesize L-proline so that the proline depleted cells can be reused (recycled) to make additional L-proline. Conditions of cultivation, workup, recovery and recycle are defined.

L-proline is a useful amino acid which is used as a medicine and in other applications. In the past, L-proline has been produced mainly by isolation from hydrolysates of proteins or gelatin or by organic synthesis. However, the yield of product obtained by these methods is very low, and the procedures involved are complicated. As a result, L-proline is one of the most expensive amino acids. Therefore, the development of a process for the mass production of L-proline using inexpensive starting materials would be highly desirable.

The fact that L-proline is contained in algae of the genus Chlorella is known. Further, it is known that L-proline is produced by the Chlorella algae in response to the environment in which it is grown, i.e., the sodium chloride content of the growth medium. The relationship between L-proline cell accumulation in *Chlorella emersonii* and the sodium chloride content of the environment external to the cell has been described in *AUST. J. PLANT Physiology* (1979) 6,69–79 in which it was reported that in the *emersonii* species of Chlorella, L-proline production within the cell generally increases as the sodium chloride concentration is increased in the environment external to the cell. However, it appears that only small amounts of L-proline are produced within *Chlorella emersonii* and, at sodium chloride concentrations higher than 335 mM, the cells plasmolyze.

The fact that Chlorella sp. 580 excrete proline also is known as reported in *Limnol. Oceanographer* (1965) 10:192–206. However, the excretion levels reported therein also are small.

Methods for producing L-proline by fermentation also are known. For example, British Pat. No. 1,132,036 discloses that L-proline can be produced from mutant strains of *Micrococcus glutamicus* by fermentation. Also, U.S. Pat. No. 4,224,409 discloses that L-proline can be obtained by culturing a mutant of the genus Brevibacterium, Corynebacterium or Microbacterium. L-proline production by fermentation, however, is somewhat expensive since the sources of carbon for use in the fermentation medium include carbon sources other than $CO_2$, such as, for example, pentoses, hexoses, dissaccharides, or the like.

Thus, even though it is known that L-proline can be produced both intracellularly and extracellularly by the genus Chlorella, insofar as applicant is aware, nothing has been reported in the literature with respect to the identification of a specific species of Chlorella and a specific method of cultivating said specific organism such that L-proline can be produced intracellularly within the organism in amounts high enough to be considered sufficient to form the basis for an industrial process.

In applicant's co-pending U.S. application Ser. No. 329,226, filed Dec. 10, 1981, entitled *Process for the Preparation of Amino Acids,* applicant has identified both a specific species of Chlorella, namely Chlorella sp. 580, and a method of cultivating the species to produce L-proline in amounts high enough to be considered sufficient to form the basis for commercial production. According to applicant's process disclosed therein, Chlorella sp. 580 is cultivated under high-intensity illumination in an aqueous growth medium containing a high concentration of sodium chloride of at least 1 M in the final stage of cultivation, in the presence of an adequate supply of carbon, in a depth not exceeding approximatley 20 cm of the aqueous medium, until algae of high L-proline content are obtained. The algae are then harvested and L-proline is thereafter recovered from the algae. While applicant's aforementined process does provide for the accumulation of high amounts of L-proline with Chlorella sp. 580 algae cells (up to approximatley 35% of the cell weight), the time typically required for cell production (cell growth) is approximatley five to seven times that required for the production of L-proline. However, it can be much longer depending on the prevailing conditions such as the amount of available sunlight when culturing is done outdoors. Thus, it would be highly desirable to reduce this ratio. One way to reduce the time contribution of the initial growth period would be to use the same cells to produce L-proline several times thereby avoiding an initial growth period for each new crop of proline produced. In order to achieve cell recycle, however, and thus reduce the time contribution of the initial growth period, the proline-rich cells must be depleted of their proline in a manner which does not destroy their proline-synthesizing capability so that the cells so depleted can be used again to produce additional amounts L-proline.

SUMMARY OF THE INVENTION

In accordance with the present invention, applicant has achieved this result by culturing Chlorella sp. 580 algae under high-intensity illumination in a aqueous growth medium containing an assimilable carbon source, assimilable nitrogen sources, inorganic salts and, if required, small amounts of organic nutrients such as vitamins, or the like, required for the growth of the algae and a high concentration of sodium chloride of at least 1 M in the final stage of the cultivation under an aerobic condition until algae of high L-proline content are obtained. The L-proline containing algae are then harvested and the L-proline thus produced is recovered from the algae without destroying or disrupting the ability of the algae to resynthesize L-proline by reducing the molarity of the sodium chloride added initially at high concentrations to achieve maximum proline enrichment of the cells. Cells made proline-rich by the addition of sodium chloride can be made to release up to 100% of their proline by simple dilution of the sodium chloride solution with water. Partial release occurs when the salt concentration is reduced to at least 0.3 M, and generally complete release occurs at dilutions of 0.14 M and below. Cells so depleted can be used again to produce a second crop of L-proline by reintroducing the cells into a high salt concentration containing medium to restimulate proline production, returning to their approximate original levels of contained proline within 16 to 48 hours, and typically within 16 to 17 hours. The entire process can be repeated again to give additional crops of L-proline from the same batch of cells.

DESCRIPTION OF THE PREFERRED EMBODIMENT

Thus, in the preferred embodiment of the present invention, there is provided a process for the recovery of L-proline from Chlorella sp. 580 algae without disrupting or destroying the L-proline synthesizing capability of the algae which comprises cultivating Chlorella sp. 580 algae under high-intensity illumination in an aqueous growth medium containing an amount sufficient of nutrients including nitrogen to effect growth of the algae and a high concentration of sodium chloride which reaches at least 1 M in the final stage of cultivation under an aerobic condition, providing an adequate supply of carbon, in a depth not exceeding approximately 20 cm of the growth medium, until algae of high L-proline content are obtained, harvesting the algae and thereafter recovering L-proline from the algae without disrupting the capability of the algae to resynthesize L-proline by diluting the harvested algae with water to a concentratin below at least 0.3 M NaCl to effect release of L-proline from the algae into the aqueous phase, removing the algae from the L-proline containing aqueous phase and reintroducing the algae into a high salt concentration containing medium of up to at least 1 M NaCl to restimulate L-proline production within the algae.

The algae used in the process of the invention are designated Chlorella sp. 580 which belong to the Class of Chlorellaceae, Order of Chlorophyta. The algae are unicellular, nonmotile, non-nitrogen fixing cells, which are round to oval in shape. The cells are approximately 5 to 10 $\mu$m in diameter and have a rigid cell wall. Under optimum conditions of cultivations, the L-proline content of each cell can be increased to approximatley 15% to 35% of the cell weight or from about 150 mg to about 350 mg per gram dry weight of algae.

Cultivation is under an adequately high-intensity of illumination and can be carried out outdoors in sunlight, or artificial light may be used if desired. If artificial light is used, the intensity of illumination should be at least 200 f.c. to 1000 f.c., and preferably 300 f.c. When cultivated outdoors, the depth of the water should not exceed about 20 cm, and the optimum depth is from about 7.5 cm to about 15 cm.

Cultivation is carried out either on an artificial medium or on sea-water adjusted so as to contain the required nutrients and salt concentration. The aqueous culture medium employed in the present invention contains an assimilable carbon source, preferably $CO_2$, assimilable nitrogen sources, conventional inorganic salts, such as, for example, the phosphates, sulfates, nitrates, chlorides and other salts of potassium, sodium, calcium, magnesium, iron, zinc, manganese, cobalt, copper, etc., and, if necessary, minor organic nutrients, such as vitamins, or the like. Such nutrients are well known in the art.

As a nitrogen source, various kinds of inorganic or organic salts or compounds such as potassium nitrate, sodium nitrate, ammonia, ammonium sulfate, ammonium chloride, ammonium nitrate, or ammonium carbonate may be used. Mixtures of these substances also may be used.

As indicated above, it is possible to use sea-water augmented by the addition of various nutrient constituents aforedisclosed, or concentrated by partial evaporation and addition of certain aforedisclosed constituents. If supplemented sea-water is used, it should have a sodium chloride content sufficient for the production of L-proline in high amounts, supplemented with a nitrogen source such as $NaNO_3$, 50 mg/l to 1.0 g/l, and a phosphate source such as $K_2HPO_4$, 15 mg/l to 300 mg/l.

There must be provided a suitable and adequate source of carbon. A 5% $CO_2$ enriched atmosphere has been found to be optimum. However, a 1% to 15% $CO_2$ enriched atmosphere can be used if desired.

Also, biotin and vitamins such as thiamine and cyanocobalamin may be used.

Cultivation is carried out under an aerobic condition, such as aerobic shaking of the culture or stirring of a submerged culture with introduction of air thereinto, at a temperature of from about 10° C. to about 40° C., preferably 25° C. to about 35° C., and at a pH of about 7.0 to about 9.0,. An optimum pH is about 8.0. The pH is advantageously adjusted by adding quantities of $CO_2$ and mineral acids such as hydrochloric acid or nitric acid as required.

The production of high quantities of L-proline in Chlorella sp. 580 algae is brought about by increasing the salinity of its growth medium. That is, the algae are cultured for a period of time in a growth medium containing a low concentratin of sodium chloride such as, for example, from about 0.25 to about 0.5 M NaCl, and preferably about 0.5 M NaCl, and then the algae are stressed by increasing the salinity of the medium whereby excess amounts of L-proline are produced within the algae cells. That is, the algae cells are salt "adapted" to grow in the presence of relatively high concentrations of sodium chloride by first culturing the algae in a medium containing a relatively low concentration of sodium chloride and thereafter increasing the sodium chloride concentration in the medium whereby the production of excess amounts of proline are stimulated within the cells.

Thus the production of L-proline can be broken down into two phases. In the first phase, or the growth phase, the algae are added to a suitable growth medium (supplemented tap or sea-water) at low density and allowed to divide and increase their cell number and mass for a period of time, normally between three to twenty-one days, until they have reached a cell density of from about 250 to about 5000 mg/l based on dry cell weight. The inoculation volume is normally between 5 and 10 volume percent of the uninoculated culture. The early culture should be grown in media which previously have been sterilized. In general, the first 20% of the inoculation chain should be accomplished using sterile media. Upon reaching the aforementioned cell density, the algae are then transferred promptly to a culture medium having a higher concentration of sodium chloride and the cells are then made proline productive by continued incubation without growth for an additional period of time of from about 6 to 80 hours, typically 16 hours. This is the second phase, or proline production phase, of the process. In lieu of transferring the algae from one medium having a lower sodium chloride concentration to a second and separate medium containing a higher sodium chloride concentration, the sodium chloride content of the original growth medium simply can be increased to a higher concentration at the end of the growth phase. For optimal growth and proline production, applicant has found that growth in the presence of approximatey 0.5 M sodium chloride followed by proline production in the presence of 1.0 M sodium chloride to yield the highest level of proline production. Although the sodium chloride concentration can be increased above 1 M in the final stage of cultivation, applicant has found thus far no significant increase in L-proline to cell ratios when the sodium chloride concentration is increased beyond 1 molar. Thus, in a more specific embodiment of the present invention, there is provided a process for the recovery of L-proline from Chlorella sp. 580 algae, without disrupting the L-proline synthesizing capability of the algae, which comprises cultivating Chlorella sp. 580 algae under high-intensity illumination in an aqueous growth medium containing an amount sufficient of nutrients including nitrogen to effect growth of the algae and a high concentration of sodium chloride of up to 0.5 M under an aerobic condition, providing an adequate supply of carbon, in a depth not exceeding approximately 20 cm of the aqueous medium for a period of time sufficient for the algae to attain a cell density of up to at least 5 grams/l and thereafter increasing the sodium chloride concentration in the medium to 1 molar and continuing cultivating the algae until algae of high L-proline content are obtained, harvesting the algae and thereafter recovering L-proline by diluting the harvested algae with water to a concentration below at least 0.3 M NaCl to effect release of L-proline from the algae into the aqueous phase, removing the algae from the L-proline containing aqueous phase and reintroducing the algae into a high salt concentration containing medium of up to at least 1 M NaCl to restimulate L-proline production within the algae.

Cells grown in the absence of sodium chloride do not become as proline productive as cells grown in the presence of sodium chloride regardless of the time allowed for the proline production cycle.

After completion of culturing and proline production, the cells are harvested (separated from the culture liquor) and the proline is recovered from the cells.

Harvesting can be accomplished by conventional methods such as sedimentation, filtration or centrifugation. Optionally, a flocculant may be added to the aqueous culture to concentrate the cells into a singular mass prior to settling or the implementation of any of the other aforementioned harvesting techniques. Alumina has been found to be a particularly effective flocculant. Suitable sources of $Al^{+3}$ flocculant are aluminum salts such as $Al(NO_3)_3.9H_2O$; $Al_2(SO_4)_3.10H_2O$; $AlNH_4(SO_4)_2.10H_2O$ and $Al_2(SO_4)_3.18H_2O$. In general, the addition of from about 5 to about 100 ppm of $Al^{+3}$ to a typical cell suspension is sufficient to bring about a 10 fold to 100 fold increase in density (g/l) of the cells. Flocculation is generally complete within 1 to 5 minutes, and essentially complete clarification of the culture liquor is achieved within 1 to 24 hours.

After harvesting, the cells are suspended in water to reduce the molarity of the sodium chloride concentration originally added in order to achieve maximum proline production. The cells are suspended in an amount of fresh water sufficient to cause release of the proline into the water phase. Applicant has found that cell concentrates made proline-rich by the addition of sodium chloride can be made to release up to 100% of their proline by simple dilution of the sodium chloride solution with fresh water. Partial release occurs when the salt concentration is reduced below 0.3 M and generally complete release occurs at dilutions below 0.14 M sodium chloride. Dilution recovery is carried out at room temperature.

The proline is recovered and purified by conventional methods such as ion-exchange chromatography, acid or alcohol extraction, thin layer chromatography, or gas chromatography and obtained in crystalline form.

Typically, amino acids other than L-proline are present in the extract or water phase following proline release from the cells. The total amount of non-proline amino acids can range up to as high as 10 weight percent with alanine typically being present in the highest amounts.

The following examples are given merely as illustrative of the invention and are not to be considered as limiting.

EXAMPLE 1

This example demonstrates that L-proline produced within Chlorella sp. 580 algae cells can be removed from the cells without disrupting the L-proline synthesizing capability of the cells.

Chlorella sp. 580 was grown in an aqueous medium containing 0.5 M NaCl, supplemented with 0.017 g/l $K_2HPO_4$, 0.340 g/l $NaNO_3$, 0.100 g/l $KNO_3$, 0.043 g/l $NaHCO_3$, 5.95 g/l $MgSO_4.7H_2O$, 4.10 g/l $MgCl_2$, 1.47 g/l $CaCl_2$, 0.00024 g/l $FeCl_3$, 0.00011 g/l $ZnCl_2$, 0.0114 g/l ethylenediamine tetraaceticacid, 0.00104 g/l $H_3BO_3$, 0.00126 g/l $MnCl_2$, 0.00000473 g/l $CoCl_2$, 0.000000266 g/l $CuCl_2$, 0.0002 g/l thiamine-HCl, 0.000001 g/l biotin, and 0.000001 g/l cyanocobalamin. The algae were grown outdoors in a 5.08 cm deep open pond (90 gallons; 342 liters) under natural conditions of solar irradiation and temperature. $CO_2$, as a carbon source, was added by constantly bubbling a slow stream of 100% $CO_2$ at a rate (120 cc/min) sufficient to provide a $CO_2$ enriched atmosphere of between 5 and 10% $CO_2$ to the pond. The pH was maintained automatically between 7.0–9.0 by the addition of $CO_2$ at the aforedescribed conditions and rate. The pond was stirred with a motorized paddle wheel with a turnover rate of 216 gallons per minute. Pond temperature varied from about 15° C. to about 21° C. The growth period was 13 days. Cell density of the culture at the end of the growth period was approximatley 500 mg/l of dry cell weight. The algae were then flocced by adding approximately 30 ppm alumina as $Al(NO_3)_3.9H_2O$ thereto, concentrated 20 fold by settling to 10,000 mg/l cells and made proline productive by increasing the sodium chloride concentration of the medium to 1 molar and incubating the algae in the presence of sunlight for approximately 48 hours in a 5% $CO_2$/air mixture. The algae were then harvested by collecting the cells as a filter cake using low pressure vacuum filtration. The filter cake was resuspended in an equal volume of water and stirred for several hours at room temperature to remove the internal proline. The cells were collected again by filtration and the washing repeated until the cells had been depleted of 83 percent of their proline. Thereafter, a 50 mg/l sample of the proline depleted cells was transferred to a 125 ml flask containing a 20 ml aliquot of the aqueous growth medium aforedescribed and 1 M NaCl. After inoculation of the medium with the algae, the algae were cultured at approximatley 30° C. for 24 hours in a 5% $CO_2$ enriched atmosphere with shaking under a bank of fluorescent lights at an average luminescence of 300 candle foot power. The lights were located approximatley 30 cm from the surface of the culture.

The pH was maintained between 7.0 and 9.0 by adding $CO_2$. After cultivation, the cells were harvested by sedimentation and the contents of the cells were examined for the presence of proline by suspending the cells at room temperature in an equal volume of water to effect release of the proline from the cells. It was found that proline had been replenished to approximately 89 percent of its original level. The results of the experiment are set forth in the Table 1 below. Proline yields were determined by thin layer chromatography.

TABLE 1

|  | mg/proline/mg cell |
|---|---|
| Cells before proline depletion | 0.12 |
| Cells after washing | 0.02 |
| Depleted cells after incubation in presence of 1M NaCl, 1% $CO_2$/air mixture and light for 24 hours. | .107 |

EXAMPLE 2

This example demonstrates the effect that the concentration of sodium chloride in the wash water used to extract proline from Chlorella sp. 580 algae has on the ability of the proline-depleted algae to resynthesize proline.

Chlorella sp. 580 algae were cultivated and made proline productive in accordance with the procedure set forth in Example 1. After incubation for 48 hours in the presence of sunlight and a 5% $CO_2$ enriched atmosphere in a 1 M NaCl aqueous medium, the cells contained approximatley 25% of their cell weight as proline. The cells were washed free of their proline by diluting 10 ml aliquot samples of the algae to 0.5 M NaCl by adding an equal volume of water to the cells. The cells were then settled to a density of 6 g/l and nine separate samples each containing 6 g/l cells were washed free of their proline content by diluting the cell suspensions 10 fold in wash water each containing a different amount of sodium chloride. The cells were shaken in air for 17 hours to allow for the maximum amount of L-proline removal. The cells were then analyzed for L-proline and then resuspended in a nutrient medium as described at 30° C. in a 5% $CO_2$ enriched atmosphere with shaking under a bank of fluorescent lights at an average luminescence of 300 candle foot power located approximately 30 cm. from the surface of the culture. The pH again was maintained between 7.0 and 9.0 by adding $CO_2$. The proline content of the cells was determined at the end of 24 hours and at the end of 48 hours by thin layer chromatography of the cell extracts. The results are set forth in Table 2 below.

TABLE 2

| Sample No. | Wash Water (NaCl Molarity) | L-proline in Cells after wash mg/proline mg/cell | L-proline resynthesized in cell after washing mg/proline mg/cell 24 hrs. | 48 hrs. |
|---|---|---|---|---|
| 1 | 1.0 | 0.250 | 0.25 | 0.25 |
| 2 | 0.5 | 0.190 | 0.125 | 0.25 |
| 3 | .306 | 0.075 | 0.188 | 0.188 |
| 4 | .289 | 0.075 | 0.188 | 0.188 |
| 5 | .259 | 0.007 | 0.188 | 0.188 |
| 6 | .233 | 0.006 | 0.188 | 0.156 |
| 7 | .203 | 0.06 | 0.06 | 0.125 |
| 8 | .172 | .00 | 0.125 | 0.125 |
| 9 | .136 | .00 | 0.031 | 0.094 |
| 10 | .095 | .00 | 0.023 | 0.023 |
| 11 | .05 | .00 | 0.015 | 0.00 |

As demonstrated by the table, proline removal became increasingly more efficient as the concentratin of sodium chloride in the wash water decreased. Reference to sample No. 3 shows that significant amounts of proline (75%) could be removed from the cells by suspending the cells in a 0.306 molar solution of sodium chloride and proline could be resynthesized in the cells by resuspending the cells in an aqueous growth medium containing 1 M NaCl.

I claim:

1. A process for the recovery of L-proline from Chlorella sp. 580 algae without disrupting or destroying the L-proline synthesizing capability of the algae which comprises cultivating Chlorella sp. 580 algae under high-intensity illumination in an aqueous growth medium containing an amount sufficient of nutrients including nitrogen to effect growth of the algae and a high concentration of sodium chloride which reaches at least 1 M in the final stage of cultivation under an aerobic condition, providing an adequate supply of carbon in a depth not exceeding approximately 20 cm of the growth medium, until algae of high L-proline content are obtained, harvesting the algae and thereafter recovering L-proline from the algae without disrupting the capability of the algae to resynthesize L-proline by diluting the harvested algae with water to a concentration below at least 0.3 M sodium chloride to effect release of L-proline from the algae into the aqueous phase, removing the algae from the L-proline containing aqueous phase and reintroducing the algae into a high salt concentration containing medium of up to at least 1 M NaCl to restimulate L-proline production within the algae.

2. A process according to claim 1, wherein said growth medium is an artificial aqueous growth medium containing:
0.017 g/l $K_2HPO_4$, 0.340 g/l $NaNO_3$, 0.100 g/l $KNO_3$, 0.043 g/l $NaHCO_3$, 5.95 g/l $MgSO_4.7H_2O$, 4.10 g/l $MgCl_2$ 1.47 g/l $CaCl_2$, 0.00024 g/l $FeCl_3$, 0.00011 g/l $ZnCl_2$, 0.0114 g/l ethylenediamine tetraacetic acid, 0.00104 g/l $H_3BO_3$, 0.00126 g/l $MnCl_2$, 0.00000473 g/l $CoCl_2$, 0.000000266 g/l $CuCl_2$, 0.0002 g/l thiamine-HCl, 0.000001 g/l biotin and 0.000001 g/l cyanocobalmin.

3. A process according to claim 1, wherein the cultivation is carried out in sunlight.

4. A process according to claim 1, wherein the cultivation is carried out in the presence of artificial light.

5. A process according to claim 4, wherein the intensity of illumination is between 200 f.c. and 1000 f.c.

6. A process according to claim 1, wherein the carbon is supplied in the form of $CO_2$ at a pH of from 7.0 to 9.0.

7. A process according to claim 1, wherein cultivation is carried out at a temperature of from between about 10° C. and about 40° C.

8. A process according to claim 1, wherein the algae are harvested by sedimentation.

9. A process according to claim 1, wherein dilution is carried out at room temperature.

10. A process for the recovery of L-proline from Chlorella sp. 580 algae without disrupting or destroying the L-proline synthesizing capability of the algae which comprises cultivating Chlorella sp. 580 algae under high intensity illumination in an aqueous growth medium containing an amount sufficient of nutrients including nitrogen to effect growth of the algae in a sodium chloride concentration of up to 0.5 M under an aerobic condition, providing an adequate supply of carbon in a depth not exceeding approximately 20 cm of the aqueous medium for a period of time sufficient for the algae to obtain a cell density of up to at least 5 g/l and thereafter increasing the sodium chloride concentration in the medium to 1 molar and continuing cultivating the algae until algae of high L-proline content are obtained, harvesting the algae and thereafter recovering from the algae without disrupting the capability of the algae to resynthesize L-proline by diluting the harvested algae with water to a concentration below at least 0.3 M sodium chloride to effect release of L-proline from the algae into the aqueous phase, removing the algae from the L-proline containing aqueous phase and reintroducing the algae into a high salt concentration containing medium of up to at least 1 M NaCl to restimulate L-proline production within the algae.

11. A process according to claim 10, wherein said aqueous growth medium is an artificial growth medium containing:

0.017 g/l $K_2HPO_4$, 0.340 g/l $NaNO_3$, 0.100 g/l $KNO_3$, 0.043 g/l $NaHCO_3$, 5.95 g/l $MgSO_4.7H_2O$, 4.10 g/l $MgCl_2$ 1.47 g/l $CaCl_2$, 0.00024 g/l $FeCl_3$, 0.00011 g/l $ZnCl_2$, 0.00114 g/l ethylenediamine tetraacetic acid, 0.00104 g/l $H_3BO_3$, 0.00126 g/l $MnCl_2$, 0.00000473 g/l $CoCl_2$, 0.000000266 g/l $CuCl_2$, 0.002 g/l thiamine-HCL, 0.000001 g/l biotin and 0.000001 g/l cyanocobalamin.

12. A process according to claim 10, wherein the cultivation is carried out in sunlight.

13. A process according to claim 10, wherein the cultivation is carried out in the presence of artificial light.

14. A process according to claim 13, wherein the intensity of illumination is between about 200 f.c. and 1000 f.c.

15. A process according to claim 10, wherein the carbon is supplied in the form of $CO_2$ at a pH up to 7.0 to 9.0.

16. A process according to claim 10, wherein said algae are cultivated in the presence of a sodium chloride concentration of up to 0.5 M for a period of time of from 3 to 21 days.

17. A process according to claim 10, wherein said algae are cultivated in the presence of a sodium chloride concentration of 1 M for a period of time of from between 6 to 80 hours.

18. A process according to claim 10, wherein cultivation is carried out at a temperature of from between about 10° C. to about 40° C.

19. A process according to claim 10, wherein the algae are harvested by sedimentation.

20. A process according to claim 10, wherein dilution is carried out at room temperature.

* * * * *

UNITED STATES PATENT AND TRADEMARK OFFICE
CERTIFICATE OF CORRECTION

PATENT NO. : 4,383,039
DATED : May 10, 1983
INVENTOR(S) : Richard I. Leavitt

It is certified that error appears in the above-identified patent and that said Letters Patent is hereby corrected as shown below:

Column 4, line 19, "9.0,." should read -- 9.0. --.

Column 10, line 4, "thiamine-HCL", should read -- thiamine-HCl --.

Signed and Sealed this

Fourteenth Day of August 1984

[SEAL]

Attest:

GERALD J. MOSSINGHOFF

Attesting Officer

Commissioner of Patents and Trademarks